(12) United States Patent
Marsman

(10) Patent No.: US 11,331,455 B2
(45) Date of Patent: May 17, 2022

(54) GUIDEWIRE KIT

(71) Applicant: Johan Willem Pieter Marsman, Hilversum (NL)

(72) Inventor: Johan Willem Pieter Marsman, Hilversum (NL)

(73) Assignee: Johan Willem Pieter Marsman, Hilversum (NL)

( * ) Notice: Subject to any disclaimer, the term of this patent is extended or adjusted under 35 U.S.C. 154(b) by 0 days.

(21) Appl. No.: 17/003,662

(22) Filed: Aug. 26, 2020

(65) Prior Publication Data
US 2021/0060309 A1    Mar. 4, 2021

(30) Foreign Application Priority Data
Aug. 28, 2019 (EP) .................................. 19194197

(51) Int. Cl.
*A61M 25/09*  (2006.01)
*A61M 25/01*  (2006.01)
*A61M 25/06*  (2006.01)

(52) U.S. Cl.
CPC ........ *A61M 25/09* (2013.01); *A61M 25/0133* (2013.01); *A61M 25/065* (2013.01); *A61M 2025/09083* (2013.01)

(58) Field of Classification Search
CPC ............ A61M 25/09; A61M 25/09041; A61M 25/09025; A61M 25/09016; A61M 25/09033; A61M 2025/09116
See application file for complete search history.

(56) References Cited

U.S. PATENT DOCUMENTS

| 4,650,472 A * | 3/1987 | Bates ..................... A61M 25/09 600/435 |
| 5,125,905 A   | 6/1992 | Wright et al. |
| 5,125,906 A * | 6/1992 | Fleck ................. A61M 25/0113 604/171 |
| 5,282,479 A   | 2/1994 | Havran |
| 9,968,761 B2* | 5/2018 | Brecker .......... A61M 25/09025 |
| 10,668,258 B1*| 6/2020 | Calhoun .............. A61B 5/0066 |

(Continued)

FOREIGN PATENT DOCUMENTS

| EP | 1570878 A2 | 9/2005 |
| EP | 1920795 A1 | 5/2008 |

(Continued)

OTHER PUBLICATIONS

European Patent Office, Extended European Search report in corresponding EP Application No. 19194197.0, dated Mar. 19, 2020 (11 pages).

(Continued)

*Primary Examiner* — Quynh-Nhu H. Vu
(74) *Attorney, Agent, or Firm* — Leydig, Voit & Mayer, Ltd.

(57) ABSTRACT

A guidewire kit including a guidewire with a shaft having a curved steering section and including a straightener bounding a lumen for straightening at least the curved deflection section of the guidewire extending into the lumen for insertion of the tip and the curved deflection section of the guidewire into a needle inserted into a vessel of a patient. The straightener is of a length of at least 8 cm for obtaining an improved and more reliable steering effect of the curved steering section.

12 Claims, 7 Drawing Sheets

(56) References Cited

U.S. PATENT DOCUMENTS

| | | | |
|---|---|---|---|
| 2004/0122416 | A1 | 6/2004 | Schweikert et al. |
| 2005/0015007 | A1* | 1/2005 | Itou .................. A61M 25/0041 |
| | | | 600/433 |
| 2009/0118707 | A1 | 5/2009 | Schweikert et al. |
| 2010/0331732 | A1 | 12/2010 | Raulerson et al. |
| 2020/0114128 | A1* | 4/2020 | Roeder ............. A61M 25/0054 |

FOREIGN PATENT DOCUMENTS

| | | |
|---|---|---|
| EP | 1992383 A1 | 11/2008 |
| EP | 2740513 A1 | 6/2014 |
| WO | WO 00/53250 A1 | 9/2000 |
| WO | WO 01/17601 A1 | 3/2001 |
| WO | WO 2008/013441 A1 | 1/2008 |

OTHER PUBLICATIONS

Mukesh Tripathi et al., "Direction of the J-Tip of the Guidewire, in Seidinger Technique, Is a Significant Factor in Misplacement of Subclavian Vein Catheter: A Randomized, Controlled Study," Anesth. Analog., 100:21-4, pp. 21-24 (2005).

Merit Medical OEM, "Guide Wires & Accessories," Brochure, MeritOEM.com, Guidewires.R3 101714, pp. 1-12.

* cited by examiner

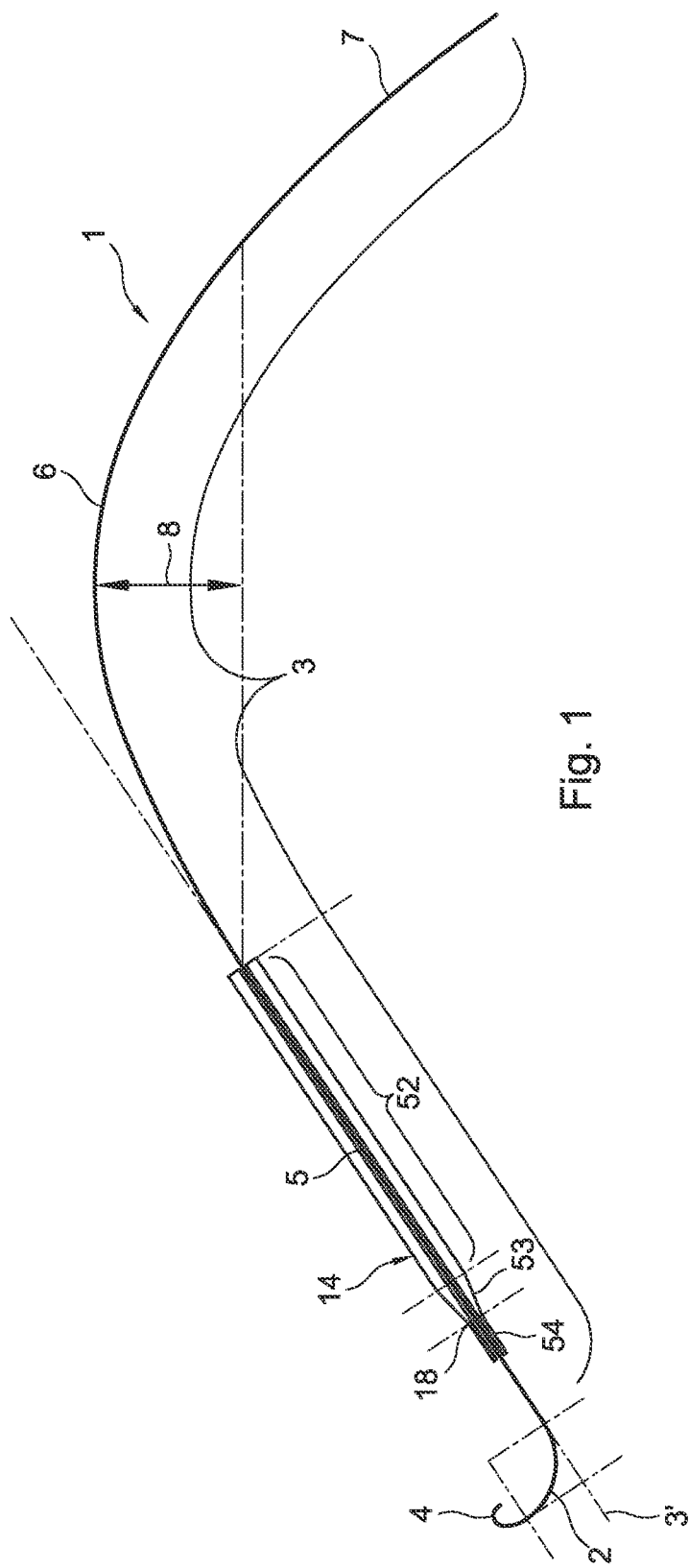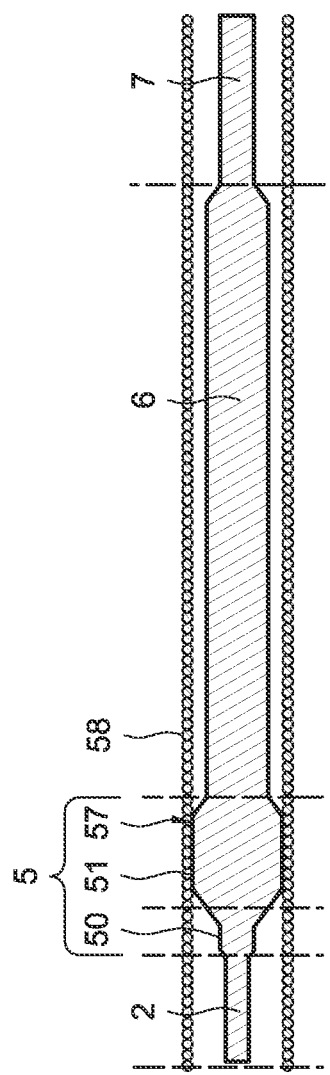

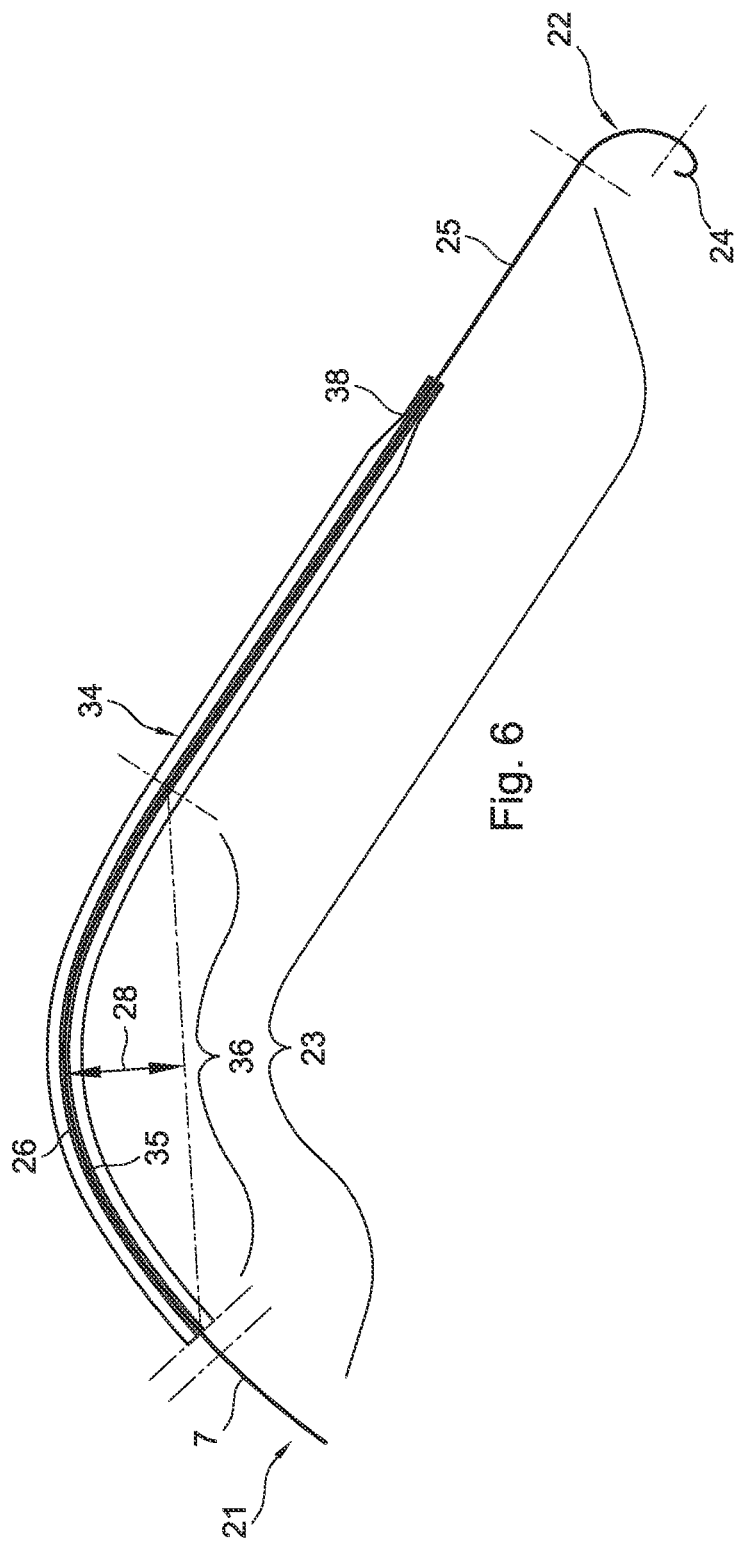
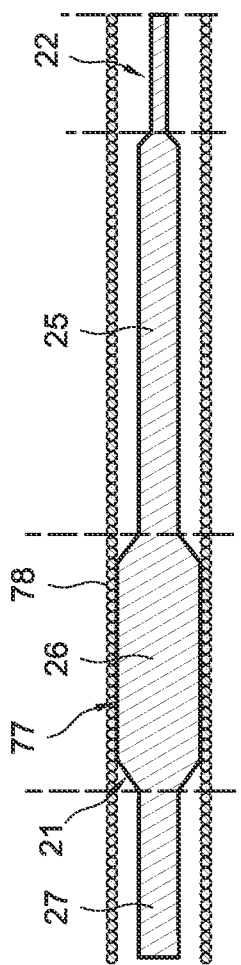

GUIDEWIRE KIT

CROSS-REFERENCE TO RELATED APPLICATIONS

This patent application claims priority to European Application No. 19194197.0, filed Aug. 28, 2019, which is expressly incorporated by reference in its entirety, including any references contained therein.

FIELD AND BACKGROUND OF THE INVENTION

The present invention relates to a guidewire kit. A guidewire is a device that is used in a number of different medical procedures to guide an implement, such as a vascular catheter, a catheter-mounted heart valve, an aortic endograft, an endotracheal tube or a gastric feeding tube, into a patient towards a desired position within the patient. Guidewires are used in a number of diagnostic and interventional fields, such as diagnostic and interventional cardiology, diagnostic and interventional neuroradiology, diagnostic and interventional radiology, urology, gastroenterology, vascular surgery, minimally invasive vascular interventions such as angioplasty, stenting, thrombolysis, transcatheter aortic valve insertion (TAVI), and endovascular abdominal aortic aneurysm repair (EVAR).

When using a conventional guidewire, a physician steers a distal end of a guidewire to a desired location inside a patient's body by pinching and torqueing a portion of the shaft section of the guidewire outside the patient's body with his fingers. The function of the shaft is transmitting rotational and longitudinal (axial) forces exerted by the physician onto the portion of the shaft section of the guidewire outside the patient's body to the distal end of the guidewire inside the patient's body.

In vascular uses, a physician is required to navigate the guidewire through the vasculature of the patient. This is done in order to position the distal end of the guidewire at a desired location. In the text, the distal end of the guidewire is the end that is to enter the patient's body. The proximal end of the guidewire is not inserted into the patient's body. The shaft of the guidewire is the section in between its proximal and distal end. Generally, the shaft is only partly inserted into the body and a part of the shaft that is not in the body is in the hands of the physician.

In other uses, a physician is required to navigate the guidewire through hollow organs, such as the urinary tract, the gastro-intestinal tract, and the bile ducts. This is done in order to position the distal end of the guidewire at a desired location. Then a diagnostic or therapeutic catheter is fed over the guidewire to the desired location for the planned intervention (e.g. dilating or stenting a narrowed duct).

The distal end of the guidewire generally has a curved deflection section at its distal end to cause the guidewire to move in a desired direction when advanced into the patient at a bifurcation or in a particularly curved vessel. The deflection section may be curved with a small radius to provide an angled tip which is oriented at an angle relative to the shaft. The shaft and the proximal end of the guidewire are straight. Positioning the distal end of the guidewire at the desired location can be tough and time consuming due to complex vascular anatomy and due to abnormalities of the vessel lumen caused by vascular disease. The physician manipulates the distal end of the guidewire through the vasculature of the patient to the desired location by pinching and torqueing the shaft of the guidewire with his fingers.

Because the positioning and steering of the distal end of the guidewire is performed under fluoroscopic guidance, a difficult and time consuming positioning procedure brings about a relatively long screening time and therefore an increased procedural radiation exposure dose imposed to the patient and to the operator. In particular in access procedures in which the guidewire is inserted through a needle inserted through the skin into a vessel of the patient to serve a guide for positioning a flexible introducer having a dilator section and a thin walled sheath and in which an operator needs to manipulate the guidewire under fluoroscopic imaging close to the access area the hands of the operator are exposed to particularly high doses of X-ray radiation.

Many efforts have been made to facilitate navigating of a guidewire tip to a location within a patient. For instance, EP 1 920 795 A1 discloses medical apparatuses, in particular stylets, for insertion into a body cavity, which have a plurality of curved sections. The curved sections are curved in different planes that intersect each other. The angle between these planes corresponds to angles between planes in which corresponding curves of lumen in the patient body are curved, so that the stylet can spontaneously assume a position in which the curved sections are located in corresponding curved portions inside the patient's body and the apparatus does not have to be steered.

EP 1 992 383 A1 discloses a guidewire with three successive curves, second and third curves being curved in opposite directions than the first and, respectively, second curves, making it difficult to erroneously enter into a side branch in a blood vessel.

WO01/17601 A1 discloses a guiding aid for an instrument to be advanced within a vascular system of which a distal end portion has first and second bent sections and optionally a short straight intermediate section in-between, so that a tip of the guidewire can more easily be guided into branchings of both large and small vessel diameters.

WO00/53250 A1 discloses a guidewire that is prepackaged in a delivery catheter, a distal end portion of the guidewire extending in a first direction up through an ipsilateral tubular extension of a graft inside the catheter and then in a second, generally opposite direction down into a contralateral tubular extension of the graft. In untensioned condition, the distal end portion has (in an order from proximal to distal) a straight main portion, a first curved portion, an intermediate portion and a second curved portion. The first and second portions can be of opposite curvature and can also define different notional planes. The intermediate portion can be straight. The double curvature allows the guidewire to be guided through the contralateral iliac artery and appropriately enter the contralateral femoral artery opposite of the femoral artery through which the catheter and the guidewire extend into the patient's body.

EP 1 570 878 A2 discloses a guidewire inserter in the form of a tubular member having a bore and a slit cutting across the wall of the tubular member. The slit gradually expands towards the proximal end, thereby forming a V-shaped aperture of a length of 5 to 100 mm in longitudinal direction of the tubular member. As the guidewire is pushed through the slit into the bore, the slit opens such that the opening gradually moves to the distal end.

US 2010/0331732 discloses a guide wire advancer for advancing a guidewire into a patient. A distal end of the advancer includes a tip configured to fit within a proximal end of an introducer. The advancer can be part of an assembly for feeding and straightening the guidewire, which assembly further includes a guidewire storage tube which is held in a coiled condition by clips. The advancer is preferably of a length of about 100 mm and is laterally open to allow thumb and forefinger access to the guidewire extending through the advancer.

SUMMARY OF THE INVENTION

It is an object of the invention to facilitate steering a guidewire with a curved deflection section at its distal end to a predetermined location inside a patient.

According to the invention, this object is achieved by providing a guidewire kit including:

a guidewire for guidance of a catheter or of a catheter introducer sheath into a human patient, the guidewire, when in untensioned condition, having:

at its distal end, a rounded tip having a radius larger than a guidewire circumference radius or a floppy tip section having more flexibility than a proximally adjacent section of the guidewire;

a curved deflection section closely proximal of the tip; and a shaft section proximal of the curved deflection section;

wherein the curved deflection section extends over an angle of curvature such that the tip is spaced from a continuation of an axis of the shaft section; and wherein the shaft section has a straight section proximally neighboring the deflection section; and a straightener bounding a lumen for straightening at least the curved deflection section of the guidewire extending into the lumen for insertion of the tip and the curved deflection section of the guidewire into a needle inserted into a vessel of a patient;

wherein the shaft section has a curved steering section proximal of the straight section;

wherein the straightener is of a length of at least 8 cm;

wherein the straightener lumen has a curved section; and wherein the curved steering section of the guidewire is at least partially located in the curved section of the lumen of the straightener if the tip of the guidewire projects from the straightener over at least one distance in a range between 5 and 15 cm.

Using a kit according to the present invention, the risk of inadvertently steering the curved deflection section of the guidewire in an unintended direction is substantially reduced, because the straightener is much longer than conventional straighteners. This causes the proximal end of the guidewire, which is curved downwards proximally of the straightener, to more reliably stay clear from a surface underneath, such as a surface of a body part of the patient, so that the risk of inadvertent exertion of forces directed sideways on the proximal end portion of the guidewire is reduced. More in particular, in use, the great length of the straightener causes the proximal end portion of the guidewire to project proximally from the straightener at a relatively high level above the point of entry of the needle into the patient, so that the likelihood of the proximal end of the guidewire touching the patient, and that thereby the steering torque exerted by gravity is disturbed, is substantially reduced.

The invention can also be embodied in a method for advancing a guidewire into a human patient through a lumen of a needle inserted into the patient, using a straightener with a lumen of which at least a portion is curved;

wherein the guidewire, when in untensioned condition, has:

at its distal end portion, a rounded tip having a radius larger than a guidewire circumference radius or a floppy tip section having more flexibility than a proximally adjacent section of the guidewire;

a curved deflection section closely proximal of the tip; and a shaft section proximal of the curved deflection section;

wherein the curved deflection section extends over an angle of curvature such that the tip is spaced from a continuation of an axis of the shaft section; and wherein the shaft section has a straight section proximally neighboring the deflection section and a curved steering section proximal of the straight section; and the method including the steps of:

straightening the distal end portion and the deflection section of the guidewire in the straightener;

positioning the straightener in line with a proximal end of the needle;

advancing the guidewire wherein the distal end portion enters the lumen of the needle; and the straightener having a curved section steering the deflection section by exerting, outside of the patient, a steering torque on a portion of the curved steering section of the guidewire located at least partially in the curved portion of the straightener.

The increased length of the straightener is also used to provide the straightener with a lumen which has a curved section and wherein a curved steering section of the guidewire is at least partially located in the curved section of the lumen of the straightener if the tip projects from the straightener over a distance up to 5-15 cm, so that the tip is still in the needle.

When the curved steering section of the guidewire is at least partially located in the curved section of the lumen of the straightener, the curvature of the steering section urges the guidewire to rotate about its central axis until the curvature assumes a position in which the portion of the curved steering section of the guidewire inside the curved section of the lumen of the straightener is least tensioned. Because the curved steering section of the guidewire is at least partially located in the curved section of the lumen of the straightener if the tip is still in the needle, it is ensured that the steering effect has started before the tip of the guidewire projects from the needle into the vessel of the patient. Thus, the deflection section of the guidewire urges the tip of the guidewire substantially into the right direction before the tip emerges from the needle.

The steering effect of the curved section of the lumen of the straightener can be operative in the same direction as the steering effect of gravity forces exerted onto a curved portion and optional more proximal portions of the guidewire projecting proximally from the straightener. However, the curved section of the lumen of the straightener also allows the straightener to be oriented about a centerline of the needle for controlled steering of the direction in which the deflection section deflects the tip. Also, the steering effect of the curved section of the lumen of the straightener can be operative in opposite direction of gravity.

In contrast to conventional guidewires, in the present invention the shaft of the guidewire is not straight over its entire length, but has a curved section thereby providing the shaft, besides with the conventional function, with additional functions that facilitate steering the guidewire to a predetermined location inside the patient by forces exerted on the guidewire section projecting proximally out of the patient.

If the curvature of the distal curved deflection section and the curvature of the curved steering section are in parallel planes, which parallel planes may be in a single common plane, the distal curved deflection section can be caused to deflect in a direction into which the curved steering section is rotated if the curved steering section and the distal curved deflection section are curved in the same direction or, the distal curved deflection section can be caused to deflect in a direction opposite to the direction into which the curved steering section is rotated if the curved steering section and the distal curved deflection section are curved in opposite directions.

Particular embodiments of the invention are set forth in the dependent claims.

Further advantages, features and details of the present invention will be elucidated on the basis of a description of one or more embodiments with reference to the accompanying drawings.

BRIEF DESCRIPTION OF THE DRAWINGS

FIG. 1 is a schematic sectional view of a guidewire kit not according to the present invention;

FIG. 2 schematically shows relative thicknesses of a core wire of the guidewire of FIG. 1;

FIG. 6 is a schematic sectional view of a second example of a guidewire kit according to the present invention;

FIG. 7 schematically shows relative thicknesses of the core wire of the guidewire of FIG. 6;

DETAILED DESCRIPTION

Figure 3:
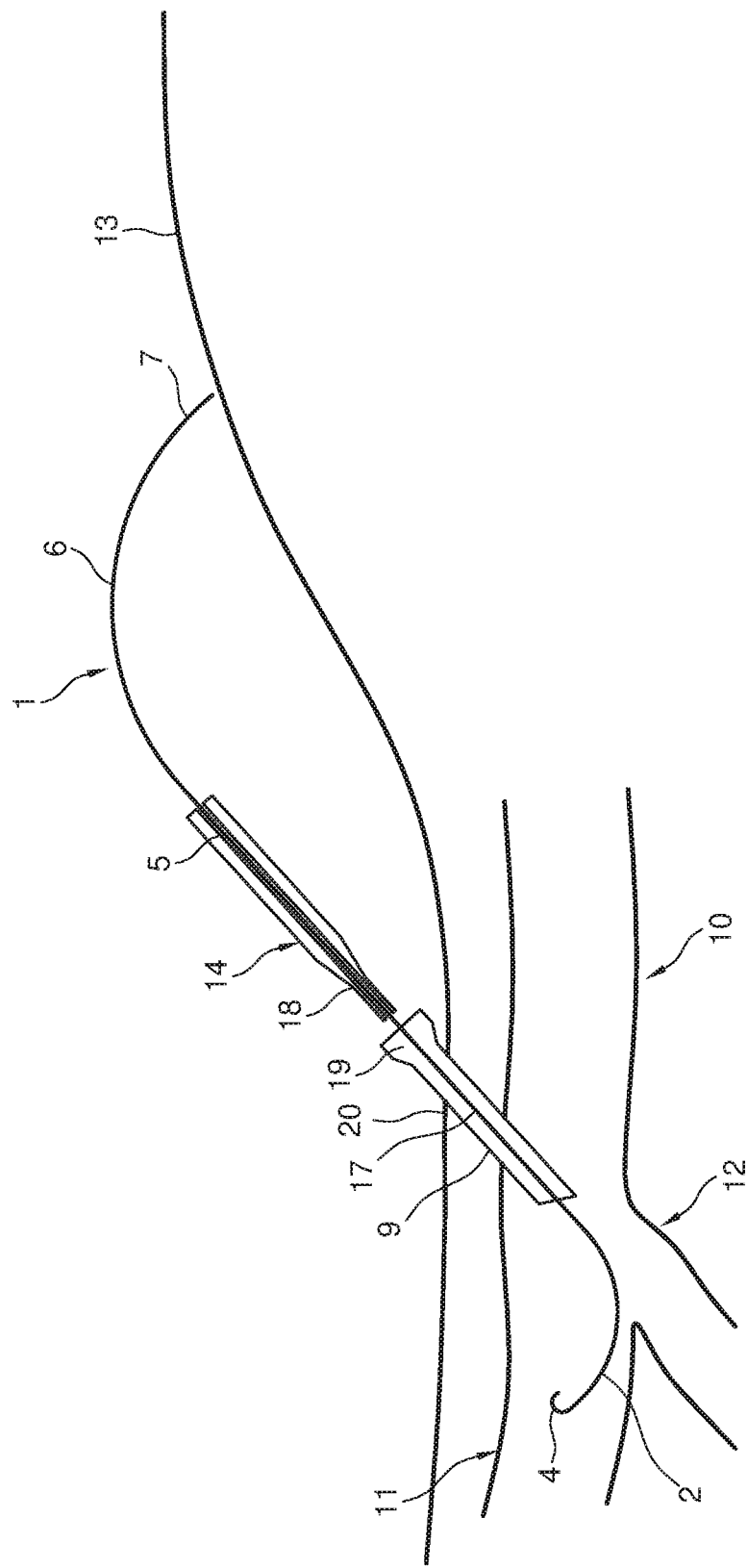
FIG. 3 is a schematic sagittal sectional view of the guidewire kit of FIG. 1 in a vascular situation wherein a tip of a distal end of the guidewire is oriented upwards.

FIGS. 1-3 show a guidewire kit not according to the invention but similar to embodiments of the invention. The kit includes a guidewire 1 and a straightener 14. In FIG. 1, the guidewire 1 is shown in untensioned condition, i.e. in a condition not subjected to loads elastically deforming the guidewire 1. In this condition, the guidewire 1 has, at its distal end, a rounded tip 4 having a radius larger than a guidewire circumference radius. In this example, the rounded tip 4 includes a curved, hook-shaped section, forming a hook that is open in a direction generally towards and along a directly adjacent section of the guidewire 1 proximally of the rounded tip 4. Instead or additionally, the tip 4 may be a floppy tip section having more flexibility than a proximally adjacent section of the guidewire. The guidewire 1 further has a curved deflection section 2 closely proximal of the tip 4 and extending over an angle of curvature such that the tip 4 is spaced from a continuation 3' of an axis of a shaft section 3 proximal of the curved deflection section 2. The deflection section 2 is curved in the same direction as the curvature of the rounded tip 4 and has an angle of curvature smaller than that of the curvature forming the rounded tip 4.

Generally, the rounded tip section 4 may for instance have a radius of 1-4 mm. The curved deflection section 2 may for instance extend over an angle of 45-165°, have a radius of 5-30 mm and/or be located at a distance of less than 5-15 mm from a proximal end of the tip 4 or located directly adjacent to a proximal end of the tip.

The shaft section 3 has a curved steering section 6 proximal of a straight section 5 proximally neighboring the deflection section 2 and a further straight section 7 proximally of the curved steering section 6. In FIG. 3, the guidewire 1 is shown in a position introduced through a needle 9 into a blood vessel 10 which bifurcates into an upper branch 11 and a lower branch 12. In the human body this vascular configuration occurs e.g. in the groin, where the Common Femoral Artery bifurcates into the Superficial Femoral Artery and the Profunda Femoral Artery.

The curvature of the curved section 6 of the shaft 3 is oriented such that the curvature has an inside facing into a direction of curvature opposite to a direction in which the deflection section 2 deflects the rounded tip section 4 from the continuation 3' of the axis of the shaft section 3. Also, the inside of the curvature of the curved section 6 of the shaft 3 is facing into the same direction as the inside of the curvature of the tip end 4 of the guidewire 1.

The straightener 14 has a tip portion 18 shaped and dimensioned to be inserted into a fitting 19 of the needle 9 so that the lumen of the needle 9 and of the straightener 14 are positioned adjacent to each other and mutually coaxially. A straightener typically has a tubular main sheath section 52 and the adjacent tip of a straightener typically has a conical section 53 tapering from the main sheath section 52 to a tubular tip sheath section 54 having a smaller outer diameter than the main sheath section 52. The diameter of the tip sheath section 54 is arranged for closely fitting in an opening of a fitting of the needle coaxially with the lumen of the needle 9. Preferably, the opening of the needle fitting is conical, tapering inwardly from a first diameter at a proximal end of the needle to a second diameter smaller than the first diameter. The outer diameter of the tip sheath section of the straightener is preferably between the first and second outer diameters of the opening in the fitting of the needle so that a tight co-axial fit in the fitting is ensured.

The straightener preferably has a lumen with a diameter providing a close sliding fit around a 0.36, 0.46, 0.89 or 1.32 mm (0.014, 0.018, 0.035 or 0.052 inch) guidewire. The straightener is preferably made of a stiff polymer material having a Young's modulus of at least 0.3 GPa such as PTFE, or PA. For obtaining a sufficiently stiff straightener, it is also preferred that the straightener has a wall thickness of at least 1 mm Preferably, the sheath portion has an outer diameter of at least 3 mm and more preferably the outer diameter is at least 4 mm. The tubular tip sheath section 54 preferably has an outer diameter of 2 mm for compatibility with fitting of standard needles.

FIG. 3 illustrates that downward normal forces exerted due to gravity onto a proximal portion of the steering section 6 and onto the straight portion 7 of the shaft 3 of the guidewire 1 cause the shaft portion 3 to rotate into a position in which the curvature of the curved steering section 6 curves downwards in proximal direction, so that the rotational position of the curvature of the steering section 6 of the guidewire 1 accommodates to the direction into which the steering section is urged by gravity. If the steering section 6 and the deflection section 2 are deviated by external force to some extent sideways, the tendency of the steering section 6 to turn downwards causes a torque to be exerted onto the guidewire 1 causing the tip 4 of the guidewire 1 to be deflected upward. Thereby the tip 4 of the guidewire is steered upwards, which causes the tip 4 of the guidewire to enter into the upper branch 11 of the blood vessel 10 when the guidewire 1 is advanced further. As is most usual in clinical practice, it is desired to steer the tip 4 into the Superficial Femoral Artery (in FIG. 3 represented by the upper branch 11 of the blood vessel 10), so the guidewire 1 can in principle simply be left to assume a rotational position imposed by gravity as shown in FIG. 3, so that ensuring that the guidewire 1 enters the Superficial Femoral Artery requires very little effort.

However, in particular when the patient has a relatively high body mass, the belly 13 may be relatively high above the point of entry of the needle 9 into the groin 20. In such situations, it can easily happen that the proximal end of the guidewire 1 touches the belly 13 of the patient. This tends to cause the proximal end of the guidewire 1 to be deviated sideways or even upwardly, which in turn causes the deflection section 2 to turn sideways or even downwardly, so that the tip 4 would not be steered reliably into the Superficial Femoral Artery 11 and the likelihood that the tip 4 of the guidewire 1 inadvertently enters the Profunda Femoral Artery 12 is increased.

Using a straightener 14 according to FIGS. 1-3, the risk of inadvertently entering the Profunda Femoral Artery 12 is substantially reduced, because the straightener 14 has a length of at least 8 cm. Because the straightener 14 is much longer than conventional straighteners, the steering section 6 and the straight section 7 project proximally from the straightener 14 at a much higher level above the point of entry of the needle 9 into the groin 20 of the patient than when a conventional straightener would be used, so that the likelihood of the proximal end of the guidewire 1 touching the belly 13 of the patient, and that thereby the steering torque exerted by gravity is disturbed, is substantially reduced.

If the kit also includes the needle 9, the needle 9 bounding a lumen 17, the length of the straightener is preferably equal to the sum of the lengths of the rounded or floppy tip 4, the deflection section 2 and the distal straight shaft section 5, minus the standard length of a puncture needle (10 cm), plus about 2-7 cm, preferably 3-5 cm. Using such a length ensures that the steering section has partially entered the straightener (over said 2-7 cm, preferably 3-5 cm) when the tip 4 of the guidewire 1 is located at the needle tip. The curved steering section 6 of the guidewire does then exert its steering torque already before the tip 4 of the guidewire 1 leaves the needle tip, so the tip is already rotated and urged into substantially the desired direction by the deflection section 2 when it enters the vessel lumen. Moreover, in that position, the straight section 5 of the guidewire 1 does not project proximally from the straightener 14, so an optimal clearance from surfaces underneath, such as a belly, is achieved.

If the straightener 14 is too long, the effect of gravity on the curved steering section stops while it is still desired for ensuring that the tip 4 is deflected into the right direction. Also, for general ease of handling a straightener should generally not be longer than 30-40 cm, If the straightener 14 is too short the object of keeping the proximal end of the guidewire 1 free from the belly of a patient is not reached or only reached to a very limited extent. In most practices a length of the straightener of 17-25 cm and more preferably 19-21 cm is preferred.

The needle lumen 17, the straightener 14 and the guidewire 1 are preferably dimensioned and shaped for bringing the straightened guidewire 1 in a position extending through the needle lumen 17, in which, if the tip 4 projects distally from the needle 9 over a distance of up to at least 3 cm and more preferably up to at least 5 cm, the curved steering section 6 is at least partially located proximally of the straightener 14. It is thus ensured that the steering effect is also maintained while the tip 4 over the guidewire 1 advances out of the needle 9 over some distance. The length of the portion of the curved steering section 6 that is located proximal of the straightener 14 if the guidewire 1 is in the indicated range of positions is preferably at least one quarter and more preferably at least one third of the length of the curved steering section 6 measured along the guidewire 1.

The physician only has to advance the guidewire 1 through the needle 9 in order to cause the tip end 4 of the guidewire 1 to enter the upper branch 11 of the blood vessel 10. In clinical practice this means that the physician does not have to steer or rotate the tip end 4 of the guidewire 1 from the Common Femoral Artery (in FIG. 3 represented by the blood vessel 10) into the Superficial Femoral Artery (in FIG. 3 represented by the upper branch 11 of the blood vessel 10), but that the guidewire 1 autonomously enters the Superficial Femoral Artery.

For this clinical use, the length of the shaft 3 may for instance be 30-80 cm or 45-65 cm, e.g. 55 cm and the length of the curved steering section 6 of the shaft 3 may for instance be (in order of increasing preference) 5-65 cm, 11-60 cm, or 20-55 cm, e.g. 40 cm, to achieve a sufficiently strong steering effect over a sufficiently large range of insertion depths at which the tip is likely to approach the bifurcation of the Common Femoral Artery at which steering in the right direction is required while also allowing the curved steering section to be bent easily into a straight configuration during and after insertion of the distal curved deflection section into the patient.

For easy accommodation to a straight shape and handling of the guidewire, in the untensioned condition, the steering section 6 preferably has a larger radius of curvature than the deflection section 2, the radius of curvature of the steering section 6 being preferably at least two, three or four times as large as the radius of curvature of the deflection section.

The length of the distal straight section 5 may for instance be 2-6 cm or 3-5 cm, e.g. 4 cm, so that the tip 4 of the guidewire 1 is near the bifurcation when the steering effect of the curved steering section is most pronounced. To allow for steering over a larger range of insertion depths, the length of the distal straight section 5, which transfers steering action from the curved steering section 6 to the curved deflection section 2, is preferably larger than 6 cm or, in order of increasing preference, at least 7, 9, 11 or 13 cm. For ease of handling and directness of steering, the length of the distal straight section 5 is preferably not more than 55 cm or, in order of increasing preference, not more than 40, 35, 25 or 20 cm.

The length of the proximal straight section 7 may for instance be 2-8 cm, e.g. 4 cm to provide a straight proximal end. For increased versatility and catheter exchange the length of the proximal straight section 7 is preferably at least 6 cm or, in order of increasing preference, at least 7, 9, 11 or 13 cm. For ease of handling the length of the proximal straight section 7 is preferably not more than 55 cm or, in order of increasing preference, not more than 40, 35, 25 or 20 cm.

The deflection section 2 of the guidewire 1 may for instance be curved as described in WO2008/013441. The largest distance 8 of the curved section 6 of the shaft 3 from a straight line between ends of the curve may for instance measure 5-12 cm or 7-10 cm, e.g. 8 cm and the angle of curvature between opposite ends of the curved section 6 may for instance be 15-45° or 20-40°, e.g. 30° to achieve a steering effect of sufficient magnitude without compromising general ease of handling of the guidewire.

In this example, the guidewire 1 has a core wire 57 and a spring wire 58 extending helically around the core wire 57 as is common in prior art guidewires. FIG. 2 shows, by way of example, relative thicknesses of the core wire 57 in the various segments 2, 5, 6, and 7 of the guidewire 1. If the relative thickness of the curved section 6 is taken to be 100%, the relative thickness of the proximal and distal straight sections 5 and 7 may for instance be 60-90%, e.g. 75%, and the relative thickness of the distal end 2 of the guidewire 1 may for instance be 30-60%, e.g. 50%. Thus, the curved steering section 6 is relatively stiff, so that a small deflection provided by the curved steering section 6 is sufficient for direct and precise steering of the distal sections 2 and 4. The core wire 57 is preferably of a shape memory alloy such as Nickel Titanium (also known as Nitinol or NiTi).

Generally, a thicker core wire is stiffer than a thinner one. In the deflection section 2 and the tip end 4 of the guidewire 1, the core wire has the smallest thickness, so that this section is the most elastic section and is very adaptable to the shape of the vessel lumen it is inserted into. The deflection section 2 should be flexible enough to prevent any harm that could be exerted by the tip end 4 of the guidewire 1.

The core wire of the curved steering section 6 of the shaft section 3 has a thickness greater than each of the thicknesses of the core wire in the proximal straight section 7 and in the deflection section 2, which makes this section stiff enough to impose a direction of curvature of the curved steering section 6, even if the steering section 6 in unloaded condition would curve upwardly in proximal direction away from the needle 9. Thus, gravity causes the guidewire 1 to rotate particularly reliably if the guidewire is released and the curvature of the curved steering section 6 is urged downwards by gravity. In turn, this rotation causes the tip end 4 of the guidewire 1 to turn to an upwardly deflected orientation and advancing the guidewire then results in the tip section 4 to enter the upper branch 11 of the blood vessel 10 as shown in FIG. 3.

The core wire of the distal straight section 5 of the guidewire 1 according to the present example has a distal portion 50 with an intermediate thickness smaller than the thickness of the core wire in the steering section 6 and larger than the thickness of the core wire in the deflection section 2. In this example, the core wire in the proximal straight section 7 has a thickness approximately identical the thickness of the core wire in the distal portion 50 of the distal straight section 5, but the thickness may also be identical to the thickness of the core wire in the curved steering section 6. Consequently, the stiffness of the distal portion 50 of the distal straight section 5 is intermediate, which is advantageous to accurately transmit the rotational orientation of the curved steering section 6 to the curved deflection section 2 of the guidewire 1. The tissues between the skin surface of the groin 20 and the lumen of the blood vessel 10 are sometimes thick due to obesity and/or dense in structure e.g. due to scars of previous surgery. It is then advantageous if, as in the present example, the straight section 5 also includes a proximal portion 51 with a stiffness that exceeds the stiffness of the steering section 6. To this end, the core wire in the proximal portion 51 of the distal straight section 5 may for instance have a thickness of 105-145%, e.g. 120% relative to the 100% thickness of the core wire in the section 6. The lengths of the proximal and distal portions 50 and 51 are preferably 25% respectively 75% of the length of the distal straight section 5. The stiffness of the proximal straight section 7 of the guidewire 1 according to the present example is also intermediate, which is advantageous for easy insertion of the proximal end of the guidewire into a port of a catheter or the like that is to be guided over the guidewire to a desired intravascular location. Also, the proximal end of the guidewire is not too stiff for using the guidewire in selected cases back to front in order to pass a tight obstruction in a blood vessel with the proximal end of the guidewire.

Figure 4:
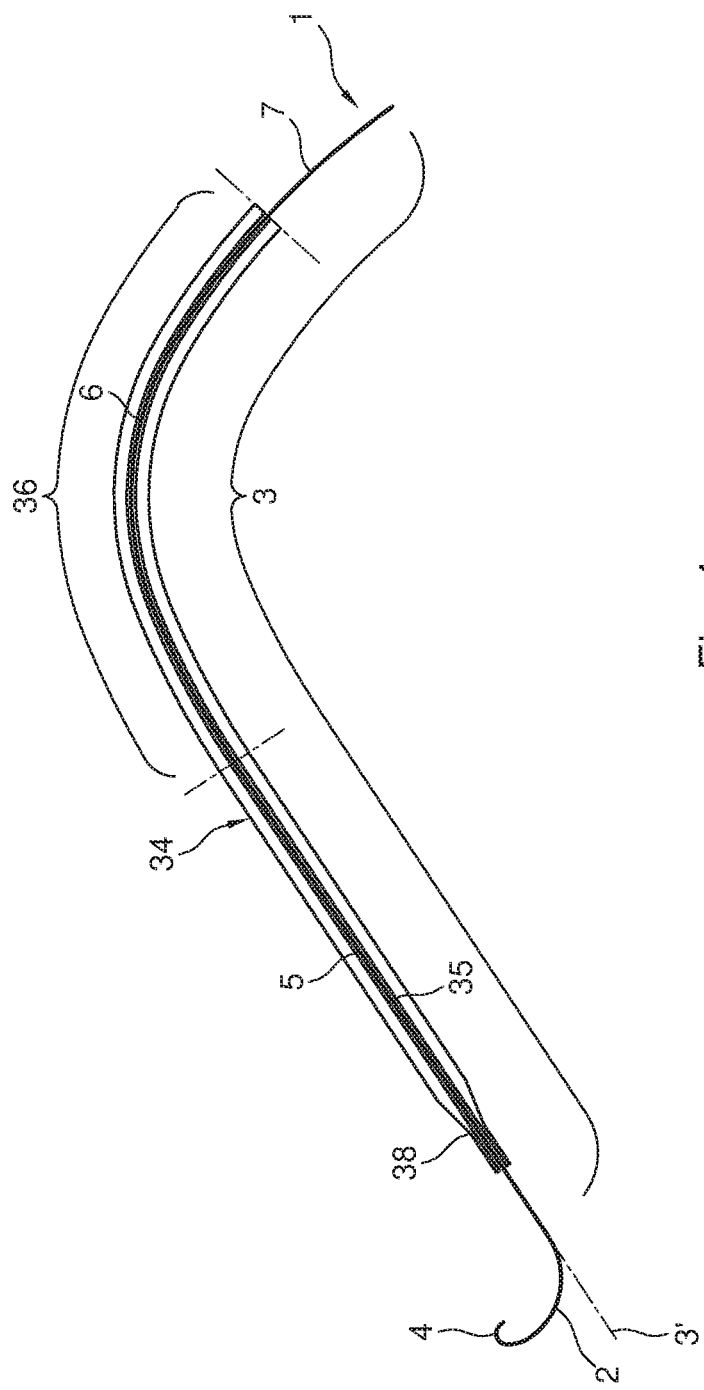
FIG. 4 is a schematic sectional view of a first example of a guidewire kit according to the present invention.
Figure 5:
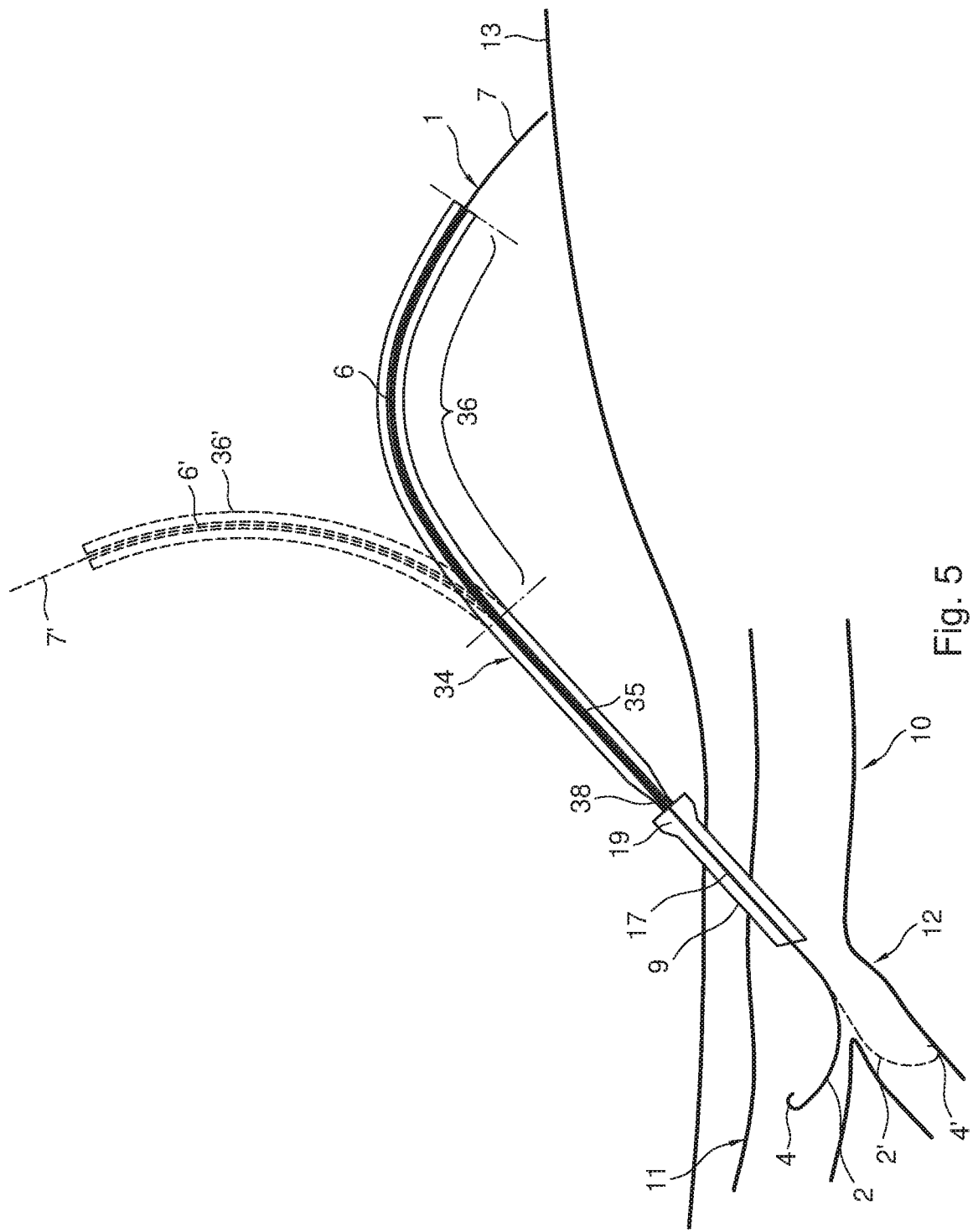
FIG. 5 is a schematic sagittal sectional view of the guidewire kit of FIG. 4 in a vascular situation wherein a tip of a distal end of the guidewire is oriented upwards.

In FIGS. 4 and 5, a first example of a guidewire kit according to the invention is shown. In general, the preferences regarding the shape and dimensions of the guidewire 1 shown in FIGS. 1-3 also apply to the guidewire 1 according to the present example. In this example, the straightener 34 has a lumen 35 which has a curved section 36. Like the straightener 14 of FIGS. 1 and 3, the straightener 34 has a tip portion 38 shaped and dimensioned to be inserted into the fitting 19 of the needle 9 so that the lumen of the needle 9 and of the straightener 34 are positioned adjacent to each other and mutually coaxially. The diameter of the lumen of the straightener is preferably the same or slightly smaller than the lumen of the needle so there is no resistance for the tip of the guidewire to cross the junction between the lumen of the tip of the straightener and the lumen of the metal part of the needle whereas the plastic fitting 19 of the needle having a considerable larger entrance diameter to facilitate introduction of the straightener into the fitting of the needle.

The curved steering section 6 of the guidewire 1 is at least partially located in the curved section 36 of the lumen 35 of the straightener 34 if the tip 4 of the guidewire projects from the straightener 34 over a distance in a range between 5 and 15 cm and preferably in a range up to 10 cm, which is the standard length of a needle via which a guidewire is introduced in an access procedure. Thus, the curved steering section 6 of the guidewire 1 is at least partially located in the curved section 36 of the lumen 35 of the straightener 34 when the tip 4 emerges from the needle 9.

When the curved steering section 6 of the guidewire 1 is at least partially located in the curved section 36 of the lumen 35 of the straightener 34, the curvature of the steering section 6 urges the guidewire 1 to rotate about its central axis until the curvature assumes a position in which the portion of the curved steering section 6 of the guidewire 1 inside the curved section 36 of the lumen 35 of the straightener 34 is least tensioned. Because the curved steering section 6 of the guidewire 1 is at least partially located in the curved section 36 of the lumen 35 of the straightener 34 if the tip 4 is at the distal end of the needle, the steering effect starts before the tip emerges from the needle 9, so it is ensured that the deflection section 2 urges the tip 4 into substantially the right direction before the tip 4 begins to project from the needle into a vessel of the patient.

In this example, the length of the straightener 34 up to the proximal end of the curved section 36 of the lumen 35 of the straightener 34 is preferably at least equal to the sum of the lengths of the rounded or floppy tip 4, the deflection section 2, the distal straight shaft section 5, minus the standard length of a puncture needle (10 cm), plus about 3-5 cm. Using such a length ensures that the steering section 6 has partially entered the curved section 36 of the lumen 35 of the straightener 34 (over said 3-5 cm) when the tip 4 of the guidewire 1 is located at the distal needle tip. The curved steering section 6 of the guidewire is then urged in the desired position by the curved section 36 of the lumen 35 of the straightener 34 before the moment at which the tip 4 of the guidewire 1 leaves the needle tip, so the tip 4 of the guidewire 1 is already rotated and urged into substantially the desired direction by the deflection section 2 when it enters the vessel lumen. If the straightener 14 is too long, the steering effect of the curved sections 6, 36 may stop while it is still desired for ensuring that the tip 4 is deflected into the right direction. If the straightener 14 is too short, the steering effect only starts after the tip 4 of the guidewire 1 has emerged from the needle or the magnitude of the steering effect will be too limited. In most practices a length of the straightener of 17-25 cm and more preferably 19-21 cm is preferred.

If the curved section 36 of the lumen 35 of the straightener 34 is curved downwardly in proximal direction and a portion of the curved steering section 6 of the guidewire is located over a short distance inside the straightener 34, the steering effect of the curved section 36 of the lumen 35 of the straightener 34 is operative in the same direction as the steering effect of gravity forces exerted onto the straight section 7 and the part of the steering section 6 that still projects proximally of the straightener 34, so the steering effects of the curved section 36 of the lumen 35 of the straightener 34 and of the forces exerted by gravity can operate in unison. However, the curved section 36 of the lumen 35 of the straightener 34 also allows the straightener 34 to be rotated about a centerline of the needle 9 for controlled steering of the direction in which the deflection section 2 deflects the tip 4. In dash-and-dot lines, the straightener 34 is shown in an orientation in which the curved section 36' of the lumen of the straightener 34 has been rotated over 180° about the centerline of the needle 9 for controlled steering the tip 4 into the lower branch 12 of the vessel 10. By rotating the straightener 34 about the centerline of the needle 9, the curved steering section 6' of the guidewire 1 is also rotated and accordingly the deflection section 2' is entrained and causes the direction in which the tip 4' is deflected to be rotated along into the Profunda Femoral artery. Thus, the straightener can also be used for torque steering of the guidewire 1.

If the kit also includes the needle 9, the needle 9 bounding a lumen 17, the needle lumen 17, the straightener 34 and the guidewire 1 are preferably dimensioned and shaped for bringing the straightened guidewire 1 in a position extending through the needle lumen 17, in which, in at least one position of the guidewire 1 in which the tip 4 is at a distal end of the needle 9 or projects distally from the needle 9, the curved steering section 6 is located at least partially in the curved portion 36 of the lumen 35 of the straightener 34.

For a particularly positive and reliable steering effect, it is preferred that, in any position of the guidewire 1 in which the tip 4 projects distally from the needle 9 over a distance of up to at least 3 cm and preferably up to at least 5 cm, the curved section 6 of the guidewire 1 is located at least partially in the curved portion 36 of the lumen 35 of the straightener 34. It is thus ensured that the steering effect is also maintained while the tip 4 of the guidewire 1 advances out of the needle 9 over some a clinically useful distance.

The length of the portion of the curved steering section 6 that is located in the curved section 36 of the lumen 35 of the straightener 34 if the tip 4 of the guidewire is located in the described positions is preferably at least one quarter and more preferably at least one third of the length of the curved steering section 6 measured along the guidewire 1.

For a strong steering and prolonged steering effect as the guidewire is advanced into the patient, it is also advantageous if the curved section 36 of the lumen 35 of the straightener 34 is shorter than the steering section 6 of the guidewire 1 and if, the curved section of the lumen of the straightener has a smaller radius of curvature than the radius of curvature of the curved steering section 6 of the guidewire 1 in the untensioned condition.

Figure 8:
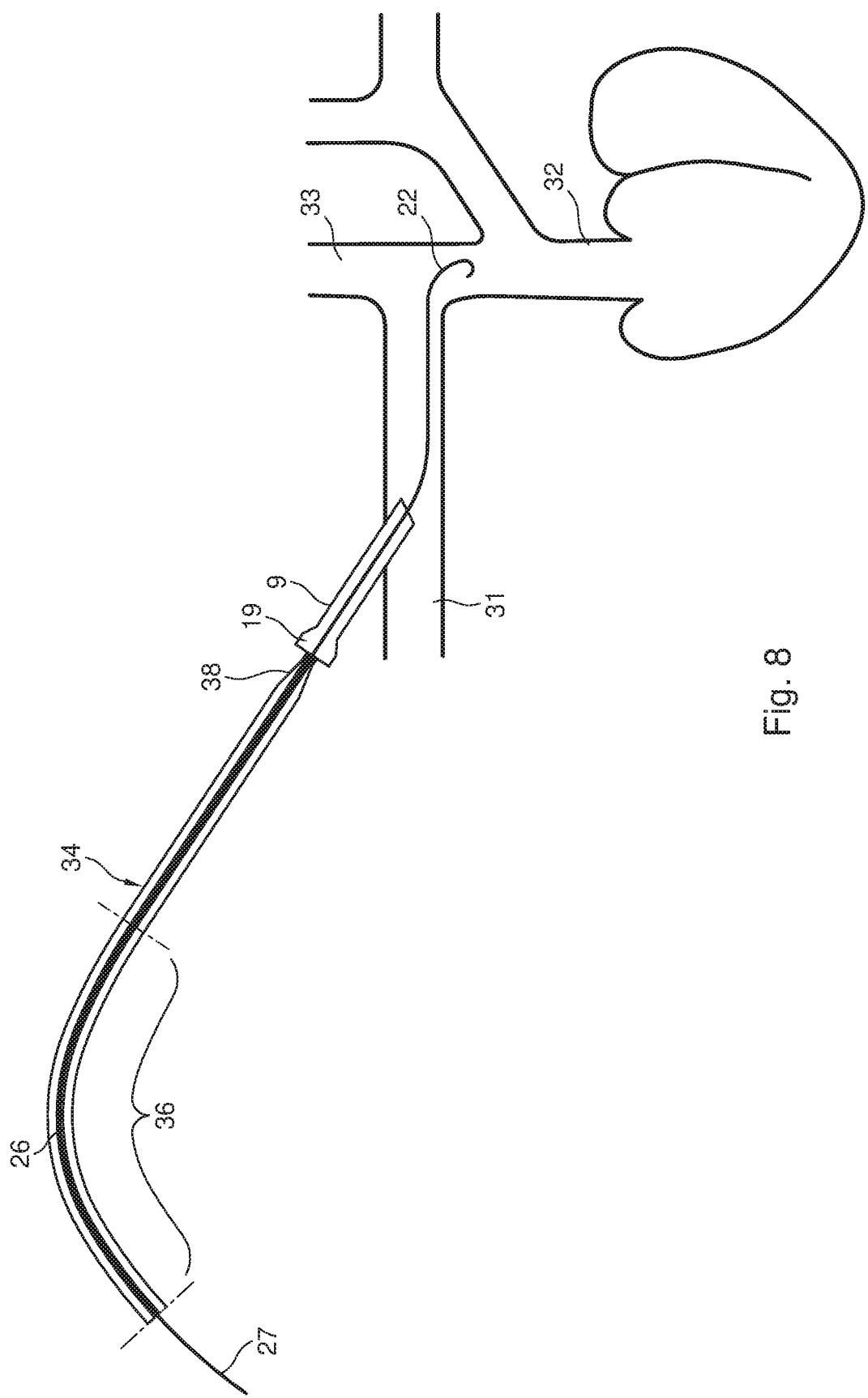
FIG. 8 is a schematic frontal sectional view of the guidewire kit of FIGS. 6 and 7 in a vascular situation wherein a tip of a distal end of the guidewire is oriented downwards.

FIGS. 6 and 8 show a frontal sectional view of a second example of a guidewire kit according to the invention. The guidewire 21 has a curved deflection section 22 and a shaft section 23 and extends through a straightener 34. The straightener 34 may be identical to the straightener 34 shown in FIGS. 4 and 5, but may also be of different dimensions as an adaptation to the different clinical use for which it is intended.

The deflection section 22 of the guidewire 21 has a tip end 24. The shaft section 23 of the guidewire 21 has a distal straight section 25, a proximal straight section 27, and a curved steering section 26 in between. The curvature of the curved section 26 of the shaft 23 is curved in the same plane and into the same direction of curvature as the curvature of the curved deflection section 22 of the guidewire 21.

The length of the shaft section 23 may be for instance 100-230 cm e.g. 160 cm and the length of the curved section 26 of the shaft 23 may for instance be 5-65 cm or 20-55 cm, e.g. 40 cm. The length of the proximal straight section 27 may for instance be 65-110 cm e.g. 85 cm and the length of the distal straight section 25 may for instance be 15-80 cm or 30-55 cm, e.g. 35 cm. The deflection section 22 of the guidewire 1 may for instance be curved as described in WO2008/013441. The largest distance 28 of the curved section 26 of the shaft section 23 from a straight line between ends of the curved section 26 may for instance measure 5-12 cm or 7-10 cm, e.g. 8 cm.

The guidewire 21 has a core wire 77 and a spring wire 78. FIG. 7 schematically shows the relative thicknesses of the core wire 77 in the various segments of the guidewire 21, which may also be similar to the example of FIG. 2.

FIG. 8 shows the guidewire 21 in a position introduced through a needle 9 into a vascular configuration that schematically represents a vascular configuration in a human thorax (seen in front view). In analogy to thoracic anatomy the needle 9 has been introduced into a right Subclavian Vein 31.

The curved steering section 26 of the guidewire 21 is at least partially located in the curved section 36 of the lumen 35 of the straightener 34 if the tip 24 projects from the needle 9. When the curved steering section 26 of the guidewire 1 is at least partially located in the curved section 36 of the lumen 35 of the straightener 34, the curvature of the steering section 26 urges the guidewire 21 to rotate about its central axis until the curvature assumes a position in which the portion of the curved steering section 26 of the guidewire 21 inside the curved section 36 of the lumen 35 of the straightener 34 is least tensioned. If the inside of the curvature of the curved section 36 of the lumen 35 of the straightener 34 is facing into the direction of the feet of the patient with the patient in prone position and a portion of the curved steering section 26 of the guidewire is located at least partially in the curved section 36 of the lumen 35 of the straightener 34, the steering effect of the curved section 36 of the lumen 35 of the straightener 34 urges the inside of the curvature of the deflection section 22 into the direction of the feet of the patient thereby deflecting the tip 24 also into the direction of the feet of the patient. However, the curved section 36 of the lumen 35 of the straightener 34 also allows the straightener 34 to be rotated about a centerline of the needle 9 for controlled torque steering of the guidewire, thereby steering the direction in which the deflection section 22 deflects the tip 24.

Since the curvature of the steering section 26 and the curvature of the deflection section 22 and accordingly the tip 24 of the guidewire are in the same direction, the deflection section 22 deflects the tip 24 into the direction of a Superior Vena Cava 32 if the steering section is curved downwards. Concurrently the tip 24 of the guidewire is deflected away from the entrance of a left Internal Jugular Vein 33. In clinical practice, in the work-up of placement of a central venous catheter, it is important that a guidewire is pointing downwards to a Superior Vena Cava because the desired position of the central venous catheter that is fed over the guidewire is in the Superior Vena Cava. However, misplacement of the central venous catheter in an ipsilateral Internal Jugular Vein is a common complication. See "Direction of the J-tip of the guidewire, in Seldinger technique, is a significant factor in misplacement of Subclavian Vein catheter: a randomized, controlled study" by Mukesh Tripathi in Anesthesia Analgesia, 2005, volume100, p. 21. FIG. 8 illustrates that the inside of the curved steering section 26 of the guidewire 21 is forced into the same direction of the main axis of extension of the body of the patient as the inside of the curvature of the curved section 36 of the lumen 35 of the straightener 34. This allows the physician to steer the distal tip 24 of the guidewire away from the right Internal Jugular Vein 33, not by rotating the guidewire about its central axis, but by holding the straightener 34 in an orientation in which the inside of the curved section 36 of the lumen 35 of the straightener 34 is curved in the direction of the main axis of extension of the body of the patient towards the feet of the patient. In fact, the physician even does not have to hold the straightener in this particular orientation but merely has to ensure that the straightener lies down more or less horizontally on the (sterilely draped) generally flat area around the patient's shoulder when the patient lies in usual prone position. Thus, the complication of misplacement of the central venous catheter in the right Internal Jugular Vein can reliably be prevented in a simple manner.

Figure 9:
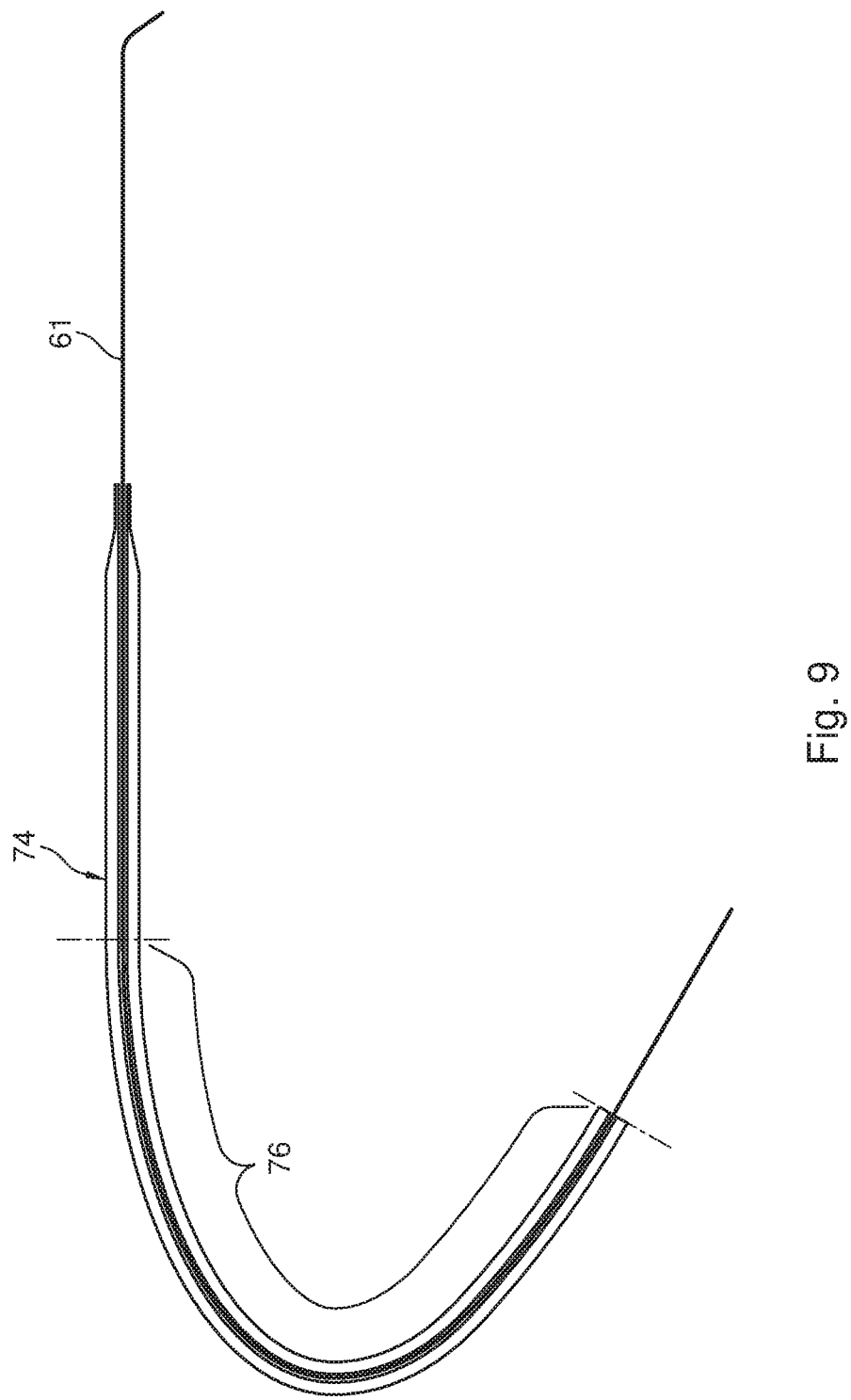
FIG. 9 is a sectional view of a third example of a guidewire kit according to the present invention.

In FIG. 9, a guidewire kit according to a third example of the invention with a guidewire 61 and a straightener 74 is shown. The curved section 76 of the lumen of the straightener 74 is curved over an angle of deflection from a straight line of about 150°, which provides a particularly positive steering effect. For this purpose, it is preferred that the angle of deflection from a straight line of the curved section 76 of the lumen of the straightener 74 is at least 45° and more preferably at least 90° or at least 120°. At the latter larger degrees of deflection, a practically useful steering effect can also be achieved if a straight guidewire is used.

The present invention is described in the foregoing on the basis of several preferred embodiments. Depending on contemplated applications, different aspects of different embodiments can be combined. This includes all combinations which can be made by a skilled person on the basis of this document. These preferred embodiments are not limitative for the scope of protection of this document. The rights sought are defined in the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A guidewire kit comprising:
   a guidewire for guidance of a catheter or of a catheter introducer sheath into a human patient, the guidewire, in untensioned condition, having:
   at a distal end, a rounded tip having a radius larger than a guidewire circumference radius or a floppy tip section having more flexibility than a proximally adjacent section of the guidewire;
   a curved deflection section closely proximal of the tip; and
   a shaft section proximal of the curved deflection section;
   wherein the curved deflection section extends over an angle of curvature such that the tip is spaced from a continuation of an axis of the shaft section; and
   wherein the shaft section has a straight section proximally neighboring said deflection section; and
   a straightener bounding a lumen for straightening at least the curved deflection section of the guidewire extending into the lumen for insertion of the tip and the curved deflection section of the guidewire into a needle inserted into a vessel of a patient,
   wherein the shaft section has a curved steering section proximal of said straight section,
   wherein the straightener is of a length of at least 8 cm,
   wherein the lumen of the straightener has a curved section, and
   wherein the curved steering section of the guidewire is at least partially located in the curved section of the lumen of the straightener if the tip of the guidewire projects from the straightener over at least one distance in a range between 5 and 15 cm.

2. The kit according to claim 1, further comprising a needle bounding a needle lumen having a length, the needle lumen and the guidewire being dimensioned for bringing the guidewire in a position extending through the needle lumen, the length of the straightener being equal to: a sum of lengths of the rounded tip or the floppy tip, the deflection section and the distal straight shaft section, minus the length of the needle lumen, plus 2-7 cm.

3. The kit according to claim 1, further comprising a needle bounding a needle lumen, the needle lumen and the guidewire being dimensioned for bringing the guidewire in a position extending through the needle lumen, wherein, if the tip of the guidewire projects distally from the needle over up to at least 3 cm, the curved steering section of the guidewire is partially located proximally of the proximal end of the straightener.

4. The kit according to claim 1, further comprising a needle bounding a needle lumen, the needle lumen and the guidewire being dimensioned for bringing the guidewire in a position extending through the needle lumen, wherein the curved steering section of the guidewire is at least partially located in the curved section of the lumen of the straightener if the tip of the guidewire is at a distal end of the needle.

5. The kit according to claim 1, further comprising a needle bounding a needle lumen, the needle lumen and the guidewire being dimensioned for bringing the guidewire in a position extending through the needle lumen, in which, if the tip of the guidewire projects distally from the needle over up to at least 3 cm, the curved steering section is located at least partially in the curved section of the lumen of the straightener.

6. The kit according to claim 1, wherein said curved section of said lumen of said straightener is shorter than said steering section of said guidewire.

7. The kit according to claim 1, wherein, said curved section of said lumen of said straightener has a smaller radius of curvature than the radius of curvature of said steering section of said guidewire in said untensioned condition.

8. The kit according to claim 1, wherein said curved section of said lumen of said straightener is curved over an angle of deflection from a straight line of at least 45°.

9. The kit according to claim 1, wherein, in said untensioned condition, said steering section of said guidewire forms a curve having a largest distance to a straight line between the ends of the curve of 5-12 cm.

10. The kit according to claim 1, said guidewire further having a core wire of a shape memory alloy and a spring wire extending helically around said core wire.

11. The kit according to claim 1, said guidewire having a core wire having a first thickness in the curved deflection section and a further thickness larger than said first thickness in the shaft section.

12. A method for advancing a guidewire into a human patient through a lumen of a needle inserted into the patient, using a guidewire kit comprising:
a guidewire for guidance of a catheter or of a catheter introducer sheath into a human patient, the guidewire, in untensioned condition, having:
at a distal end, a rounded tip having a radius larger than a guidewire circumference radius or a floppy tip section having more flexibility than a proximally adjacent section of the guidewire;
a curved deflection section closely proximal of the tip; and
a shaft section proximal of the curved deflection section;
wherein the curved deflection section extends over an angle of curvature such that the tip is spaced from a continuation of an axis of the shaft section; and
wherein the shaft section has a straight section proximally neighboring said deflection section; and
a straightener bounding a lumen for straightening at least the curved deflection section of the guidewire extending into the lumen for insertion of the tip and the curved deflection section of the guidewire into a needle inserted into a vessel of a patient,
wherein the shaft section has a curved steering section proximal of said straight section,
wherein the straightener is of a length of at least 8 cm,
wherein the lumen of the straightener has a curved section,
wherein the curved steering section of the guidewire is at least partially located in the curved section of the lumen of the straightener if the tip of the guidewire projects from the straightener over at least one distance in a range between 5 and 15 cm, and
wherein the method comprises:
straightening the distal end portion and the deflection section of the guidewire in the straightener;
positioning the straightener in line with a proximal end of the needle;
advancing the guidewire wherein the distal end portion enters the lumen of the needle; and
steering, with the straightener having a curved section, the deflection section by exerting, outside of the patient, a steering torque on a portion of the curved steering section of the guidewire located at least partially in the curved portion of the straightener.

* * * * *